(12) United States Patent
Schwind et al.

(10) Patent No.: US 11,169,160 B2
(45) Date of Patent: Nov. 9, 2021

(54) DEVICE AND METHOD FOR DETECTING BLOOD GROUP ANTIGENS BY MEANS OF AN INCOMPLETE ANTIBODY

(71) Applicant: GRIFOLS DIAGNOSTIC SOLUTIONS INC., Emeryville, CA (US)

(72) Inventors: Peter Schwind, Fribourg (CH); Ariane Caesar, Wuennewil (CH)

(73) Assignee: GRIFOLS DIAGNOSTIC SOLUTIONS INC., Emeryville, CA (US)

(*) Notice: Subject to any disclaimer, the term of this patent is extended or adjusted under 35 U.S.C. 154(b) by 685 days.

(21) Appl. No.: 15/312,365

(22) PCT Filed: May 23, 2015

(86) PCT No.: PCT/EP2015/001067
§ 371 (c)(1),
(2) Date: Nov. 18, 2016

(87) PCT Pub. No.: WO2015/180834
PCT Pub. Date: Dec. 3, 2015

(65) Prior Publication Data
US 2017/0122968 A1    May 4, 2017

(30) Foreign Application Priority Data
May 26, 2014   (DE) .................... 10 2014 007 851.5

(51) Int. Cl.
*G01N 33/558*   (2006.01)
*G01N 33/80*    (2006.01)
*G01N 33/559*   (2006.01)

(52) U.S. Cl.
CPC ........... *G01N 33/80* (2013.01); *G01N 33/558* (2013.01); *G01N 33/559* (2013.01)

(58) Field of Classification Search
CPC ..... G01N 33/80; G01N 33/558; G01N 33/559
See application file for complete search history.

(56) References Cited

U.S. PATENT DOCUMENTS 4,861,711 A * 8/1989 Friesen ................ G01N 33/558
                                                    435/7.92
4,943,522 A    7/1990 Eisinger
(Continued)

FOREIGN PATENT DOCUMENTS

CA    1334825 C    3/1995
CN    1438486 A    8/2003
(Continued)

OTHER PUBLICATIONS

Cummerrow et al., *Apheresis product identification in the transplant center: development of point-of-care protocols for extended blood typing of stem cell apheresis products*, Bone Marrow Transplant (2012), 47(6):860-5.
(Continued)

*Primary Examiner* — Christopher L Chin
(74) *Attorney, Agent, or Firm* — Knobbe, Martens, Olson & Bear LLP

(57) ABSTRACT

The invention relates to a device for determining a cellular-bound analyte in a liquid sample, comprising a separation matrix with at least one indicator zone. The invention is characterized in that the indicator zone comprises a first antibody directed against the cellular-bound analyte or a fragment thereof and a binding element directed against the first antibody, the first antibody being an incomplete antibody. The separation matrix is preferably designed in the form of the membrane of a lateral flow assay device or as a gel matrix. In a particularly preferable manner, the device comprises a membrane (2) with a charging zone (5) for applying the liquid sample, at least one indicator zone which can interact with the cellular-bound analyte, and at least one (Continued)

Figure 1:
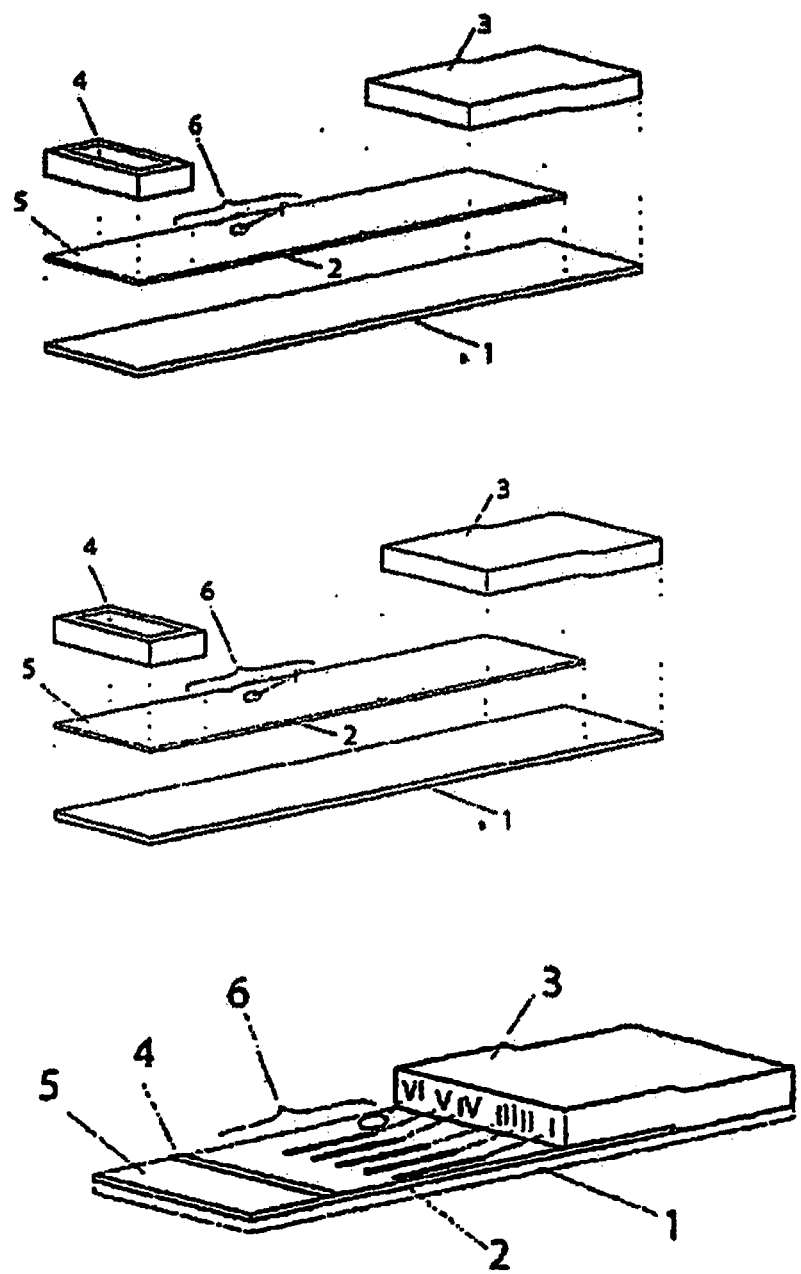

absorption region (3) which absorbs the liquid after passing the indicator zone. The indicator zone lies between the charging zone (5) and the absorption region (3). The invention is characterized in that the indicator zone comprises an antibody directed against the cellular-bound analyte or a fragment thereof and a binding element directed against the first antibody, the first antibody being an incomplete antibody.

17 Claims, 3 Drawing Sheets

(56) References Cited

U.S. PATENT DOCUMENTS

| | | | | |
|---|---|---|---|---|
| 5,338,689 | A | * | 8/1994 | Yves ................ G01N 33/5304 422/504 |
| 5,780,248 | A | * | 7/1998 | Milchanoski ......... B01L 3/5021 422/72 |
| 7,745,228 | B2 | * | 6/2010 | Schwind .............. G01N 33/558 436/164 |
| 8,053,226 | B2 | * | 11/2011 | Schwind .............. G01N 33/558 435/287.1 |
| 8,841,082 | B2 | * | 9/2014 | Schwind .............. G01N 33/558 435/283.1 |
| 2006/0270064 | A1 | * | 11/2006 | Gordon ................ G01N 33/80 436/518 |
| 2007/0042499 | A1 | * | 2/2007 | Schwind .............. G01N 33/558 436/164 |
| 2007/0248983 | A1 | * | 10/2007 | Schwind .............. G01N 33/558 435/7.1 |
| 2010/0136585 | A1 | * | 6/2010 | Schwind .............. G01N 33/558 435/7.25 |
| 2011/0076698 | A1 | | 3/2011 | Wang | |

FOREIGN PATENT DOCUMENTS

| | | |
|---|---|---|
| CN | 1816746 A | 8/2006 |
| CN | 201053966 Y | 4/2008 |
| CN | 101606065 A | 12/2009 |
| CN | 101957370 A | 1/2011 |
| DE | 36 86 474 T2 | 2/1993 |
| DE | 103 30 982 A1 | 2/2005 |
| EP | 0 223 978 B1 | 8/1992 |
| EP | 0223978 B | 8/1992 |
| JP | S 61-271455 A | 12/1986 |
| JP | H 01-501819 A | 6/1989 |
| JP | 2001-133457 A | 5/2001 |
| JP | 2005-502872 A | 1/2005 |
| JP | 2008-241251 A | 10/2008 |
| JP | 2009-513939 A | 4/2009 |
| JP | 2010-515030 A | 5/2010 |
| JP | 2011-522228 A | 7/2011 |
| JP | 2013-174612 A | 9/2013 |
| RU | 2 456 619 C2 | 7/2012 |
| WO | WO 2003/023354 A2 | 3/2003 |
| WO | WO 2005/003787 A1 | 1/2005 |
| WO | WO 2005/005986 | 1/2005 |
| WO | WO 2005/005991 | 1/2005 |
| WO | WO 2005/005991 A1 | 1/2005 |
| WO | WO 2008/080544 | 7/2008 |
| WO | WO 2008/080544 A1 | 7/2008 |

OTHER PUBLICATIONS

Salama, et al., *Rapid detection of antibodies to immunoglobulin A molecules by using the particle gel immunoassay*, Vox Sanguinis (2001) 81, 45-48.
Notice of Reasons for Rejection, dated Feb. 5, 2018, in Japanese application No. JP2016-564216.
Office Action, dated Jun. 20, 2018, in Chilean Application No. 2016-03038.
Office Action, dated Sep. 18, 2017, in Chinese Application No. 201580027408.0.
Office Action, dated Feb. 28, 2018, in Chinese Application No. 201580027408.0.
Patent Search Report, dated Oct. 31, 2018, in Russian Application No. 2016142888/04(068662).
Langston M.M. Evaluation of the gel system for ABO grouping and D typing // Transfusion, vol. 39, pp. 300-305, 1999.
Cummerow et al., Apheresis Product Identification In The Ninguna Transplant Center: Development Of Point-Of-Care Protocols For Extended Blood Typing Of Stem Cells Apheresis Products, Bone Marrow Transplantation, vol. 47, No. 6, pp. 860-865, 2012.
Salama A et al., Rapid Detection Of Antibodies To Immunoglobulin A Molecules By Using The Particles Gel Immunoassays, Vox Sanguinis. vol. 81, No. 1, pp. 45-48, 2001.

* cited by examiner

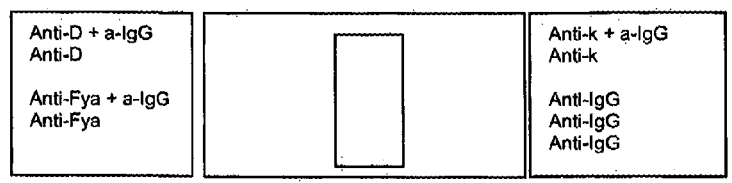
Fig. 3A
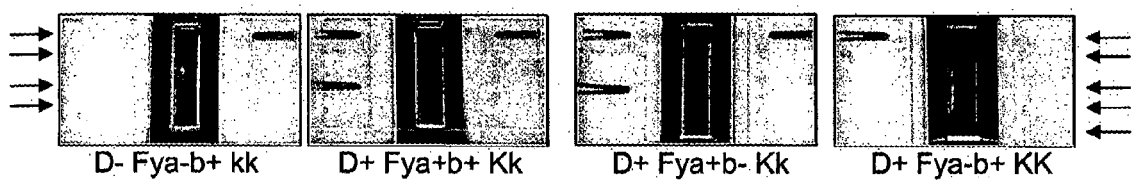
| Fig. 3b | Fig. 3c | Fig. 3d | Fig. 3e |

DEVICE AND METHOD FOR DETECTING BLOOD GROUP ANTIGENS BY MEANS OF AN INCOMPLETE ANTIBODY

CROSS REFERENCE TO RELATED APPLICATIONS

The present application is a U.S. national stage entry under 35 U.S.C. § 371 of PCT International Application No. PCT/EP2015/001067, which was filed on May 23,2015, which claims priority to German Patent Application No. 10 2014 007 851.5, which was filed on May 26, 2014, the disclosures of each of which are incorporated by reference herein in their entireties.

FIELD OF THE INVENTION

The invention relates to devices and methods for determining blood group antigens by means of an incomplete antibody, in particular for simultaneously determining blood group antigens.

PRIOR ART

In blood group serological diagnostics, parameters which are important especially in connection with transfusions or haemolytic disease of the newborn are generally detected. This includes inter alia the detection of antigens on the surface of erythrocytes which are characteristic for the blood groups. Further important antigen systems are also found on thrombocytes, granulocytes and lymphocytes, which likewise play a role in transfusion and/or transplantation.

It is known that, in order to determine the blood group antigens, the erythrocytes of the person to be tested (donor or recipient) are brought together with reagents which contain blood-group-specific antibodies. The tests are usually liquid tests, in which a test batch is produced by mixing an erythrocyte-containing sample with a sample containing antibodies directed against a specific blood group feature. The test batch is then incubated for a defined period of time and under defined conditions and, when the incubation is complete or directly after a centrifugation step, the batch is checked either visually or by optical methods for possible agglutination or adsorption of the erythrocytes. The prevailing end-point measurement in blood group serology continues to be haemagglutination. Direct agglutinating antibodies are also referred to as complete antibodies in blood group serology. Antibodies which cannot agglutinate erythrocytes directly are analogously referred to in blood group serology as incomplete antibodies.

The simultaneous determination of blood group antigens using a lateral flow test format is known from WO 2005/005991. The examples of WO 2005/005991 disclose the determination of blood group antigens by means of IgM antibodies, which are complete antibodies and lead directly to haemagglutination. The WO specification does not, however, disclose the determination of blood group antigens using an incomplete antibody with the aid of a lateral flow test.

Lateral flow tests are widely used nowadays as rapid tests, for example as pregnancy tests, for determining infection markers or as a drug screen. A lateral flow test arrangement consists of a solid carrier to which there is applied an work zone for the sample to be tested, a separating membrane on which binding elements, for example capture antibodies or antigens, are bound and on which binding reactions can be detected, and an absorbent absorption region which allows the sample to be tested to flow through the separating membrane.

Test membranes of conventional lateral flow tests are generally described having chromatography-like separation. The analyte in the sample binds specifically to the binding elements fixed in a membrane, which are generally arranged as indicator zones in bands located one behind the other or one above the other. The binding complex is made visible by indicator particles, which are generally already present in the arrangement in dried form in a conjugate release pad. The conjugate release pad is typically disposed between the work zone and the membrane. The pre-coated coloured indicator particles are coated, for example, with an antibody directed against the analyte being sought.

The most important blood group features which nowadays must routinely be clarified in pre-transfusion tests on the patient and on donors are: A, B, D, C, E, c, e, Cw, K, k, Jka, Jkb, Fya, Fyb, M, N, S, s, P1, Lea, Leb, Kpa, Kpb, Lua, Lub. The antigens or antigen epitopes to be tested are, by way of example, those of the ABO blood group system, of the Rh, Kell, Lewis-Hh, Duffy-Kidd, MNS, Lutheran and P system, of the blood group systems Diego, Yt, Scianna, Dombrock, Colton, Chido/Rodgers, Gerbich, Cromer, Knops, Landsteiner-Wiener, Xg, Kx, Indian, Ok, Raph, John Milton Hagen, Langereis, Sid, FORS, JR and/or LAN, in particular A1, A2, AB, B, D, C, c, E, e, Cw, K, k, M, N, S, s, Jka, Jkb, Fya, Fyb, Kpa, Kpb, Jsa, Jsb, Lea, Leb, Lua, Lub, P1, I, H, Xga, U, Vw, Wra, Lan, Vel, Dia and/or Mia.

Because of their negative net surface charge and the zeta potential thereby exerted, erythrocytes have a natural statistical minimum distance of approximately 300 angstroms between the cells.

That minimum distance can be bridged by antibodies of the IgM class in physiological medium because of the molecule size, but naturally not by antibodies of the IgG class. This means that, as a rule, only IgM-class antibodies are available in blood group serology for a direct end-point measurement by haemagglutination. Direct agglutinating antibodies are also referred to as complete antibodies in blood group serology (most IgM antibodies are complete antibodies).

According to the current prior art, blood groups generally cannot be detected by means of IgG antibodies by direct haemagglutination. Antibodies which cannot agglutinate erythrocytes directly are referred to analogously in blood group serology as incomplete antibodies (most IgG antibodies are incomplete antibodies).

This leads to the situation that it is necessary to work with so-called different phases and reaction times and temperatures according to whether (monoclonal) IgMs or, on the other hand, monoclonal IgGs or polyclonal antibodies are available for detection for a particular blood group property, which makes harmonised or homologised working procedures more difficult.

Provided that IgM antibodies are available, direct determination with haemagglutination as the end point is frequently possible without the admixture of further antibodies or intensifiers or proteolytic enzymes and without incubation (immediate spin). With the widely used gel technique, incubation is not necessary for the performance of such a test; the reaction mixture comprising the erythrocytes to be tested and the antibody reagent simply has to be pipetted into the work zones of the gel card and centrifuged for 9-10 minutes in a neutral physiological medium, that is to say a physiological medium which does not contain antibodies (for example DG Gel Neutral Card from Diagnostic Grifols).

In another variant of the same technique, blood-group-specific antibodies of the IgM class have already been introduced into the gel matrix. The erythrocytes to be tested then simply have to be pipetted into the work zones of the gel card (for example DG Gel ABO RH (2D) from Diagnostic Grifols).

If the antibody available for determining a particular blood group feature does not belong to the IgM class, a technique/phase change is required in order to make haemagglutination possible as the end point. This is the case, for example, for the following of the above-mentioned features, for which no commercially available IgM antibodies are available according to the current prior art: k, Fya, Kpa, Kpb and Lua. The following further features are likewise of interest, such as Dia, Jsa, Jsb, Coa, Cob, Wra, Xga. Commercial monoclonal IgM antibodies are not available for detecting any of these antigens.

Since IgG antibodies are generally not capable of overcoming the distance that is present between two erythrocytes due to natural repulsion, reaction with an antigen-specific IgG antibody can achieve only sensitisation (that is to say antibody binding, but not haemagglutination, therefore no diagnostic end point) of the cells that are positive for the particular antigen, without the visible end point of haemagglutination, which in turn is necessary for simple visual diagnostic detection: If, for example, an erythrocyte which carries the blood group feature Duffy a (Fya) is incubated with an anti-Fya antibody of the IgG class, the antibody-antigen reaction (sensitisation) occurs, but this does not lead to the visible end point of haemagglutination. In order to achieve this, the sensitised cells must additionally be incubated with a class-specific antibody (in the present case anti-IgG), with the aid of which the cells sensitised with IgG antibodies can be bridged and the end point of haemagglutination can be produced (indirect Coombs test). The gel technique, which is widely used for this purpose, requires an incubation time of 10-15 minutes at 37° C. for this test, with subsequent centrifugation for 9-10 minutes in an anti-human globulin or Coombs card (for example DG Gel Coombs Card from Diagnostic Grifols).

In the tube technique, which is likewise widely used, incubation prior to centrifugation for approximately 20 seconds is not necessary in the case of immediate spin. For the indirect Coombs test, incubation is first carried out for from 15 to 60 minutes at 37° C. with the blood-group-specific incomplete antibody, following which a plurality of washing steps are required before the anti-human globulin reagent is added and centrifugation is then carried out for 20 seconds.

There is therefore a need for a device and a method for determining cell-bound analytes, in particular blood group antigens, for which no standardised IgM antibodies, in particular no commercially available IgM antibodies, are available. There is further a need for a device and a method for simultaneously determining at least two cell-bound analytes, wherein a standardised IgM antibody such as a commercially available antibody is available for only one of the two cell-bound analytes, so that the determination of both analytes in the prior art requires a phase or technique change.

SUMMARY OF THE INVENTION

According to a first aspect of the present invention, there is provided a device for determining a cell-bound analyte in a liquid sample, comprising a separating matrix having at least one indicator zone, characterised in that the indicator zone comprises a first antibody directed against the cell-bound analyte, or a fragment thereof, and a binding element directed against the first antibody, the first antibody being an incomplete antibody.

According to a preferred embodiment, the device comprises a membrane (2) having an work zone (5) for application of the liquid sample, at least one indicator zone which is able to interact with the cell-bound analyte, and at least one absorption region (3) which absorbs the liquid after it has passed through the indicator zone, the indicator zone being situated between the work zone (5) and an absorption region (3), characterised in that the indicator zone comprises a first antibody directed against the cell-bound analyte, or a fragment thereof, and a binding element directed against the first antibody, the first antibody being an incomplete antibody.

According to a further preferred embodiment, the device contains tubes filled with gel material. The gel technique is used to determine the agglutination reaction of erythrocytes. The gel column acts as a filter which slows or stops the migration of the agglutinated erythrocytes relative to non-agglutinated erythrocytes and thereby effects separation. According to the invention, the indicator zone of the gel contains an antibody directed against the cell-bound analyte, or a fragment thereof, and a binding element directed against the first antibody, the first antibody being an incomplete antibody.

According to a second aspect of the present invention, there is provided a device for simultaneously determining a first and a second cell-bound analyte in a liquid sample, comprising a membrane (2) having an work zone (5) for application of the liquid sample, at least two indicator zones which are able to interact with the cell-bound analytes, and at least one absorption region (3) which absorbs the liquid after it has passed through the indicator zone, the indicator zones being situated between the work zone (5) and the at least one absorption region (3), characterised in that (i) the first indicator zone comprises a first antibody directed against the first cell-bound analyte, or a fragment thereof, and a binding element directed against the first antibody, the first antibody being an incomplete antibody, and (ii) the second indicator zone (a) comprises a first antibody directed against the second cell-bound analyte, the first antibody being a complete antibody; or (b) comprises a first antibody directed against the second cell-bound analyte, the first antibody being incomplete, and a binding element directed against that antibody.

Surprisingly, the inventors of the present application have found that, by applying a first incomplete antibody and a second antibody directed against the first antibody together in an indicator zone, it is possible to configure a device having a separating matrix, preferably in the form of the membrane of a lateral flow test device or as a gel matrix, in such a manner that it is possible to determine a cell-bound analyte by means of an incomplete antibody as the first antibody. As a result, it is possible for the first time to determine a cell-bound analyte, for which no standardised, such as commercially available, antibodies of the IgM type are available, using a separating matrix such as a lateral flow test device. This results in a considerable shortening of the time required for determining such analytes, which previously could generally be determined only by means of the indirect Coombs test, which requires an additional incubation step. The procedure according to the invention is also surprising for the skilled person because he would have assumed that, for example when using anti-IgG molecules as the second antibody, these were neutralised by the non-analyte-specific IgG molecules present in a high concentration in whole blood.

It was therefore not possible in the prior art to determine two blood group antigens simultaneously (that is to say in a single lateral flow device or in a single gel card having a plurality of gel tubes for determining a plurality of parameters), the first being determined by an IgG antibody and the second by an IgM antibody, without a technique or phase change thereby being required. The present invention therefore offers the advantage of simultaneous determination using a single lateral flow set-up, which requires only a single homogeneous method step without different media and different incubations.

According to a third aspect of the present invention, there is provided a method for producing the above devices, comprising applying a first antibody directed against a cell-bound analyte, or a fragment thereof, and a second antibody directed against the first antibody, or a fragment thereof, wherein the first antibody is an incomplete antibody.

According to a fourth aspect of the present invention, there is provided a method for determining at least one cell-bound analyte, comprising applying a first antibody directed against a cell-bound analyte, or a fragment thereof, and a binding element directed against the first antibody in the indicator zone, wherein the first antibody is an incomplete antibody.

According to a fifth aspect of the invention, there is provided the use of the devices according to the invention for analysing blood, in particular for determining blood group antigens or antigen epitopes.

DETAILED DESCRIPTION OF THE INVENTION

Definitions

In connection with the present invention, the following expressions are to have the meanings given below:

The expression "complete antibody" means an antibody which leads to the agglutination of erythrocytes in the physiological saline medium. Complete antibodies include IgM antibodies or fragments thereof, provided the fragments are still capable of agglutination. The IgM antibodies can be monoclonal or polyclonal.

The expression "incomplete antibody" means an antibody which, when incubated with erythrocytes, does not lead to the agglutination thereof. Incomplete antibodies include IgG antibodies, IgA antibodies, IgD antibodies and IgE antibodies including their subclasses or antibody fragments, provided the fragments are still capable of binding a second antibody directed against the entire antibody. These antibodies can be monoclonal or polyclonal. Methods of producing antibodies of the various classes are known to the skilled person.

The expression "cell-bound analyte" means any molecule that is naturally bound to the surface of a cell, preferably of a human cell, in particular of an erythrocyte. They include, for example, receptors or blood group antigens, blood group antigens being preferred.

The expression "blood group antigen" includes antigens of the ABO blood group system, of the Rh, Kell, Lewis-Hh, Duffy-Kidd, MNS, Lutheran and P system, of the blood group systems Diego, Yt, Scianna, Dombrock, Colton, Chido/Rogers, Gerbich, Cromer, Knops, Landsteiner-Wiener, Xg, Kx, Indian, Ok, Raph, John Milton Hagen, Langereis, Sid, FORS, JR and/or LAN, in particular A1, A2, AB, B, D, C, c, E, e, Cw, K, k, M, N, S, s, Jka, Jkb, Fya, Fyb, Kpa, Kpb, Jsa, Jsb, Lea, Leb, Lua, Lub, P1, I, H, Xga, U, Vw, Wra, Lan, Vel, Dia and/or Mia.

Production of the Lateral Flow Device

A method that is suitable in principle for producing a lateral flow device is described in DE 10330982 A1 and WO 2005/005986, but it is altered as indicated hereinbelow. The disclosure of DE 10330982 A1 and WO 2005/005986 is incorporated herein by reference.

The method for producing a device according to the invention comprises applying a first antibody directed against a cell-bound analyte, or a fragment thereof, and a binding element directed against the first antibody in the indicator zone, wherein the first antibody is an incomplete antibody.

The first antibody directed against a cell-bound analyte and the binding element directed against the first antibody can be applied to the membrane in the region of the indicator zone either together or separately from one another. Where they are applied separately from one another, it is preferred that a drying step takes place after the application of the first antibody, before the binding element is applied. The concentration of the first antibody is determined empirically and depends on the affinity for the cell-bound analyte. The concentration of the binding element can be optimised by test series on the basis of the concentration of the first antibody and the properties thereof.

The analyte to be determined is preferably a blood group antigen. The first antibody is particularly preferably directed against a cell-bound analyte selected from the blood group antigens A, B, AB, D, C, E, c, e, Cw, K, k, Jka, Jkb, Fya, Fyb, M, N, S, s, P1, Kpa, Kpb, Lua, Lub, Lea, Leb, Mia, Dia, Jsa, Jsb, Coa, Cob, Wra and Xga, particularly preferably against k, S, Fya, Kpa, Kpb, Lua, Lea, Leb, Mia, Lua, Lub, Dia, Jsa, Jsb, Coa, Cob, Wra and Xga. The first antibody is an incomplete antibody in this case, preferably an IgG or IgA antibody, particularly preferably an IgG antibody. For example, the following antibodies can be used: anti-Fya: clone P3TIM (Merck Millipore, VL); anti-S: clone P3S13JS123 (Diagast, ref. 78007); anti-k: clone P3A118OL67 (Merck Millipore, FA); and anti-D: clone ESD-1 (Alba Bioscience).

The binding element is preferably selected from an antibody directed against the first antibody, or a fragment thereof, and a lectin or a fragment thereof. The antibody directed against the first antibody is particularly preferably an anti-IgG antibody. Anti-IgG antibodies are commercially available, particularly preferred are the clone MS-278 (Merck Millipore) and as a polyclonal antibody, for example, mono-type or anti-IgG anti-human globulin (Medion Grifols Diagnostics). Where the first antibody is an IgA antibody, the second antibody is an anti-IgA antibody. Anti-IgA antibodies are commercially available. The anti-IgG or anti-IgA antibodies can be of the IgM or IgG type, a monoclonal anti-IgG of the IgM class being preferred. Preferred lectins are protein A and protein G.

Where a device for simultaneously determining a first and a second cell-bound analyte according to the second aspect of the present invention is to be produced, (i) the first indicator zone comprises a first antibody directed against the first cell-bound analyte, or a fragment thereof, and a binding element directed against the first antibody, wherein the first antibody is an incomplete antibody, and (ii) the second indicator zone comprises (a) a first antibody directed against the second cell-bound analyte, wherein the first antibody is a complete antibody; or (b) a first antibody directed against the second cell-bound analyte, wherein the first antibody is incomplete, and a binding element directed against that antibody.

The first cell-bound analyte is preferably selected from the blood group antigens k, Fya, Kpa, Kpb, Lua, Lub, Mia, Dia, Jsa, Jsb, Coa, Cob, Wra, Xga and S and the second cell-bound analyte is preferably selected from A, B, AB, C, D, E, c, e, Cw, K, Lea, Leb, Jka, Jkb, Fyb, P1 and s.

The first antibody directed against the second cell-bound analyte according to alternative (a) is a complete antibody, in particular an IgM antibody, which leads directly to haemagglutination. The first antibody directed against the second cell-bound analyte according to alternative (b) is an incomplete antibody, preferably the first antibody according to alternative (b) is an IgG or IgA antibody. The binding element directed against the first antibody according to alternative (b) permits determination by haemagglutination. The binding element is preferably an IgG or IgM antibody. Alternatively, a lectin such as protein A or protein G may also be used.

The membrane of the device used according to the invention is a porous membrane. Preferred membrane materials are, for example, nitrocellulose (for example UniSart from Sartorius, HiFlow from Millipore, Whatman, AE99 or FF85/100 from Whatman Schleicher & Schuell), polyethylene (Lateral Flo from Porex Corporation) or nylon (Novylon from CUNO). The membrane preferably has as large a pore size as possible, since a high porosity of the membrane facilitates the penetration in particular of cell components of the sample to be determined, for example of erythrocytes, into the porous structure. The use of absorbent membranes is particularly advantageous. However, the device according to the invention is not limited to those properties. Preference is given to any membranes having a high capillary flow rate, where the capillary flow rate is the time [s] required for a dye solution to cover a distance of 40 mm on a given membrane. Membranes whose capillary flow rate is <100 are particularly preferred.

In a preferred embodiment of the invention, a sealing element is arranged on the porous membrane downstream, in relation to the direction of flow, of the work zone of the device according to the invention. Two- or three-dimensional sealing elements are used, which are placed on the porous membrane and with which a sample work zone separated from the remainder of the surface of the porous membrane is created. According to the invention, the sealing element acts primarily as a liquid barrier and permits the directional distribution of sample liquid and test reagents into the porous membrane. According to the invention, the sealing element further seals off the sample work zone in order to prevent liquid from undesirably entering the other regions of the lateral flow device.

Preferred embodiments of the sealing element are the web or trough or funnel shape. The sealing element is cut the material used to produce the sealing element. In the case of the funnel or trough shape, the sealing element is provided with an inner opening, preferred variants of which are round, square or rectangular shapes which, in the case of the funnel shape, taper towards the underside (membrane contact side) of the sealing element. Preferred materials for the sealing element are materials which do not absorb water (hydrophobic). In a particular embodiment, the materials are coated on one side with an adhesive film, for example a pressure-sensitive or self-adhesive acrylate adhesive. The sealing element can thus be bonded directly to the surface of the porous membrane. Alternatively, the sealing element can be connected, for example adhesively bonded, to the lateral flow casing, the lateral flow casing in this embodiment pressing the sealing element on the surface of the porous membrane and the functions of the sealing element thereby being achieved.

Preferred materials for forming two-dimensional sealing elements are any form of adhesive tape or adhesive foil (for example Tesa 4124 from Beiersdorf AG, ARcare 7815 from Adhesives Research). Preferred materials for forming three-dimensional sealing elements are flexible, closed-pore elastomer materials or flexible silicone materials with different material thicknesses, preferably 3-5 mm (for example EPDM140 cellular rubber from Pitzner, silicone rubber or solid rubber, hardness 40 deg. or less, from Castan).

In a further preferred embodiment, multiple sealing elements consisting of one piece with, for example, 20 individual cavities (trough shape) are arranged on one membrane.

As a result of this design, the device according to the invention is capable of absorbing liquid samples which contain cells, such as whole blood, without thereby filtering off the cells. Furthermore, the sealing element allows large sample volumes to be applied to the porous membrane (work zone) without flooding it. The sealing element thus supports the use of the absorbing properties of the porous membrane. Furthermore, the sealing element ensures a directional sample flow. The device according to the invention can, however, function well with or without a sealing element.

For the absorption region (absorption pad) of the device according to the invention, preference is given to mechanically stable materials, preferably having water absorption capacities of 20-30 g/100 $cm^2$ (for example Millipore). The contact between the absorption pad and the lateral flow membrane of the device according to the invention is established by pressure and overlapping with the porous membrane. Precise positioning of the absorption pad on the membrane is achieved by adhesively bonding the absorption pad to the backing sheet carrying the lateral flow membrane.

In a further embodiment, the components of the device according to the invention are applied to a substrate or backing sheet for the purposes of mechanical strengthening. The device according to the invention can, however, function with or without a backing sheet. Preference is given to mechanically stable materials which do not absorb water, preferably with material thicknesses of 100 µm or more, which are coated on one side or on both sides with an adhesive film, for example a pressure-sensitive or self-adhesive acrylate adhesive (for example 0.005" polyester W/GL-187, G&L). The porous membrane and the absorption pad are fixed to the backing sheet. In the case of a backing sheet that is adhesive on both sides, the adhesive second side is used for fixing the stack to further surfaces, for example inside the lateral flow casing.

In a further embodiment, the device according to the invention, either with or without a backing sheet to which the components of the device according to the invention are applied, is integrated in a casing, the membrane components thereby being pressed against one another and the casing supporting the function of the sealing element. The device according to the invention can, however, function equally as well with or without a casing in this case.

Determination Methods

The method is carried out by applying a liquid sample. The liquid sample preferably consists of blood or constituents of blood, particularly preferably of whole blood, erythrocyte concentrate, coagulated blood or test liquid, such as control blood. The sample may be diluted with a buffer in this case before it is applied.

The invention will be explained in greater detail below by means of figures and examples, without being limited thereto.

FIG. 1 is, by way of example, a perspective view of a device according to the invention for lateral flow tests for simultaneously determining blood group antigens. In the present example, the device consists of a backing sheet 1, the porous membrane 2, the absorption pad 3 and the sealing element 4, which is two-dimensional in web form or three-dimensional in trough form. The porous membrane 2 is thereby fixed to the backing sheet 1 provided with a pressure-sensitive or self-adhesive acrylate adhesive. The absorption pad 3 is likewise fixed to the backing sheet 1, some of the absorption pad 3 overlapping the porous membrane 2. The sealing element 4 fixed to the upper side of the porous membrane 2 separates the work zone 5 from the remainder of the membrane surface and permits the directional distribution of sample liquid and test reagents into the porous membrane 2. The indicator zone region 6 is arranged between the work zone 5 and the region of the porous membrane 2 that is in contact with the absorption pad 3.

Figure 2:
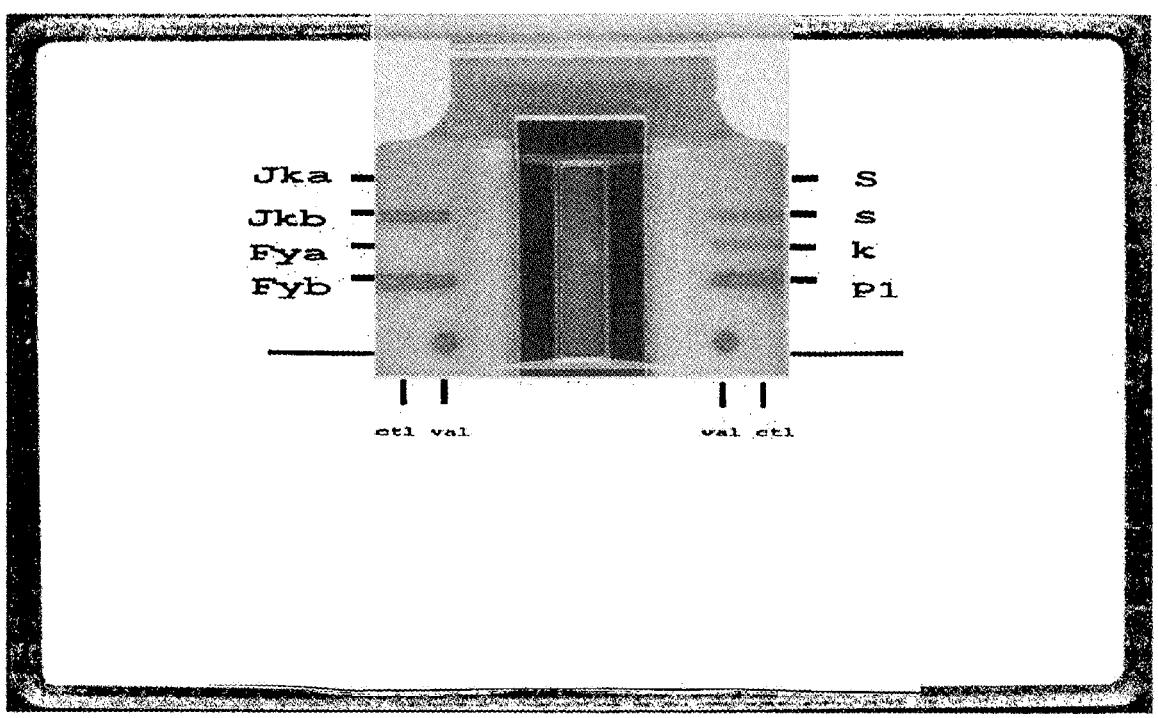

FIG. 2 shows a successful simultaneous determination of the blood group antigens Jka, Jkb, Fya, Fyb, S, s, k and P1. The donor is Jka−Jkb+Fya−Fyb+S−s+k+P1+. The sample was hereby applied to the work zone situated in the middle. The sample flows through both the indicator zones situated to the left of the work zone and the indicator zones situated to the right of the work zone.

FIG. 3 shows a comparison of, on the one hand, the method according to the invention with a first IgG antibody directed against the blood group antigens D, Fya and k and a second anti-IgG antibody directed against the first antibody, and, on the other hand, a comparative method without the second antibody. On the right-hand side, anti-IgG is applied three times as a further negative control. FIG. 3a shows the dispensing plan used. FIGS. 3b to 3e show the experimental results which were obtained using samples from different donors.

EXAMPLES

Example 1

Blood Group Determination

Production of the Test Strips:

The test strips consist of an work zone located in the middle of the membrane, as well as two indicator zone regions and two absorption regions at equal distances on both sides of the central work zone. Membranes of the Millipore HiFlow Plus 065 type are trimmed in strips to a size of 19×48 mm (width/length; x/y) for an 8- to 10-band design and adhesively bonded to a backing sheet (for example from G&L). Two absorption pads (Millipore) measuring 19×17 mm and overlapping the membrane by 7 mm are adhesively bonded to the ends of the membrane distal to the work zone. 6 mm-long bands (each 0.6 µl) of solutions of different blood-group-specific antibodies are applied to the indicator zone regions, so as to be offset in two linear rows, using a dispenser, for example AD3200 (Biodot):

anti-Jka: clone P3HT7 (Diagast, ref. 78003); anti-Jkb: clone P3 143 (Diagast, ref. 78004); anti-Fya: clone P3TIM+ anti-IgG clone MS278 (Merck Millipore, VL+JZ); anti-Fyb: clone SpA264LBg1 (Merck Millipore, FF); anti-S: clone P3S13JS123+anti-IgG clone MS278 (Diagast, ref. 78007+ Merck Millipore, JZ); anti-s: clone P3BER (Merck Millipore, FE); anti-P1: clone P3MON2 (Merck Millipore, VN); anti-k: clone P3A1180L67+anti-IgG clone MS278 (Merck Millipore, FA+JZ). All the antibodies are concentrated about 10 times before formulation.

The anti-Jka antibody is positioned to the left of the work zone in position x=3 mm/y=9 mm to y=15. Three other antibodies (anti-Jkb, anti-Fya and anti-Fyb) are dispensed iteratively at intervals of x=2.5 mm in parallel with the position of the anti-Jka antibody. The anti-S antibody is positioned to the right of the work zone in position x=3 mm/y=34 mm to y=40. Three other antibodies (anti-s, anti-k and anti-P1) are dispensed iteratively at intervals of x=2.5 mm to the position of the anti-S antibody.

The anti-erythrocyte-specific validation antibody (Val=process control; rabbit IgG fraction of anti-human RBC, Rockland, 209-4139) is applied as a dot in x=2.5 mm/y=3 mm offset to the last band of the series of the blood-group-specific antibodies. The control dot (Ctl=negative control; contains all the constituents of the various antibody formulations with the exception of the antibody) is applied in y=3 mm offset to the Val dot. All the antibody solutions contain 1% BSA and 9.4% APP3 solution [32.4% (w/v) D(+)-trehalose dihydrate, 0.055% (v/v) Genapol PF10, 21.8% (v/v) methanol, PPB buffer: 15 mM potassium phosphate buffer/10 mM NaCl/0.05% (w/v) NaN$_3$]. The antibodies are diluted in 0.07M Tris/HCl buffer, having a pH of 7, with the exception of anti-P1, which is diluted in 0.01 M citrate buffer, having a pH of 4, as follows: anti-Jka 1:5, anti-Jkb 1:5, anti-Fya 1:5+anti-IgG 1:25, anti-S 1:5+1:100, anti-s (small) 1:16.7, anti-k 1:10+anti-IgG 1:100, anti-P1 1:10 and anti-RBC 1:10. After the antibodies have been dispensed, the membranes are dried for 1 hour at 45° C. and welded together with a sealing element in a polycarbonate casing (Medion Grifols Diagnostics AG).

Test Set-Up:

The blood samples can be taken in tubes containing conventional anticoagulants (for example EDTA, CPDA-1, ACD, citrate) or in native form.

In a test tube, 1 drop (50 µl) of anticoagulated whole blood is mixed with 4 drops (200 µl) of Diluent F (Medion Grifols Diagnostics) or 1 drop of erythrocyte sediment is mixed with 8 drops (400 µl) of Diluent F, or 2 drops (100 µl) of the cells of coagulated blood are mixed with 2 drops of Diluent F.

Two drops (100 µl) of the resulting suspension are applied to the work zone of the described test arrangement. After 30 seconds, 6 drops (300 µl) of Diluent F are applied to the work zone. After 5 minutes, the results are read off and recorded.

Result:

The test is valid if the anti-RBC validation dot (val) shows a clearly positive signal (red dot) and the control dot (ctl) indicates a negative result. The presence of a red band indicates that the tested blood sample is positive for the particular blood group feature. The absence of a band in the corresponding position in the work zone means that the tested blood sample is negative for the corresponding blood group feature.

FIG. 2 shows the successful simultaneous determination of the blood group antigens Jka, Jkb, Fya, Fyb, S, s, k and P1. The donor is Jka−Jkb+Fya−Fyb+S−s+k+P1+.

Example 2

Blood Group Determination by Means of the Method According to the Invention and Comparative Example The test strip was produced analogously to Example 1. There were used as antibodies: anti-D, clone ESD-1 (Alba), human IgG; anti-k (cellano), clone P3A118OL67 (Millipore), human IgG; anti-Fya, clone P3TIM (Millipore), human IgG, and as the second antibody: anti-IgG, clone MS278 (Millipore), mouse IgM.

FIG. 3a shows the dispensing plan used. FIGS. 3b to 3e show the experimental results obtained with samples from different donors. It can clearly be seen that only the determination by means of a first antibody of the IgG class directed against the blood group antigen and a second antibody directed against that first antibody leads to a clearly detectable band, whereas the determination using the first antibody of the IgG class does not lead to a clearly recognisable band. On the right-hand side, anti-IgG is applied three times as a further negative control. FIGS. 3b to 3e show that no band was obtained in the case of this negative control.

The invention claimed is:

1. A device for determining presence of at least one cell-bound analyte in a liquid sample, comprising:
    a separating matrix in the form of a porous membrane,
    an absorption pad, wherein a portion of the absorption pad is in contact with a portion of the porous membrane,
    a work zone for application of the liquid sample,
    the porous membrane having at least one indicator zone, wherein the indicator zone comprises a first antibody, or a fragment thereof, directed against the cell-bound analyte, and a binding element directed against the first antibody, the first antibody being an incomplete antibody, wherein the cell-bound analyte is a blood group antigen, and wherein the indicator zone is part of the porous membrane and situated between the work zone and the portion of the porous membrane that is in contact with the absorption pad,
    wherein the absorption pad is positioned in the device to absorb the liquid sample after it has passed by lateral flow through the at least one indicator zone, the at least one indicator zone being situated between the work zone and the at least one absorption pad, such that when the at least one cell-bound analyte is present in the liquid sample, the at least one cell-bound analyte forms a complex with the first antibody, or a fragment thereof, in the indicator zone as an indication of the presence of the at least one cell-bound analyte.

2. The device according to claim 1, wherein the first antibody is an antibody of the IgG or IgA type.

3. The device according to claim 1, wherein the binding element directed against the first antibody is selected from an antibody directed against the first antibody, or a fragment thereof, and a lectin or a fragment thereof.

4. A method for producing a device according to claim 1, comprising:
    applying a first antibody, or a fragment thereof, directed against the cell-bound analyte, and a binding element directed against the first antibody in the indicator zone, wherein the first antibody is an incomplete antibody.

5. The method for producing a device according to claim 4, wherein the first antibody and the binding element are applied separately from one another or as a mixture.

6. A method for determining at least one cell-bound analyte, comprising:
    applying the sample to the work zone of a membrane of the device according to claim 1, wherein said sample is present in an amount sufficient to cause the sample liquid to flow by lateral flow through the indicator zones towards the absorption region (3), the indicator zones comprising a first antibody, or a fragment thereof, directed against the cell-bound analyte, and to cause the cell-bound analyte in the sample liquid to form a complex with the first antibody, or a fragment thereof, in the indicator zones;
    visually detecting formation of the complex in the indicator zones.

7. The method according to claim 6, wherein the method does not comprise incubating the cell-bound analyte with an antibody before the cell-bound analyte is applied to the membrane.

8. The method according to claim 6, wherein the liquid sample comprises blood or constituents of blood selected from the group consisting of whole blood, erythrocyte concentrate, coagulated blood, and control blood sample.

9. A method for determining blood group antigens or antigen epitopes comprising the device according to claim 1, the method comprising:
    applying a sample to the work zone of a porous membrane, wherein said sample is present in an amount sufficient to cause the sample liquid to flow by lateral flow through the indicator zones towards the absorption pad, the indicator zones comprising a first antibody, or a fragment thereof, directed against the blood group antigens or antigen epitopes, and to cause the cell-bound analyte in the sample liquid to form a complex with the first antibody, or a fragment thereof, in the indicator zones;
    visually detecting formation of the complex in the indicator zones.

10. A method for simultaneously determining one or more of blood group antigens selected from the group consisting of A, B, AB, D, C, E, c, e, Cw, K, k, Jka, Jkb, Fya, Fyb, M, N, S, s, P1, Kpa, Kpb, Lua, Lub, Lea, Leb, Mia, Dia, Jsa, Jsb, Coa, Cob, Wra and Xga or antigen epitopes comprising the device according to claim 1, the method comprising:
    applying a sample to the work zone of a porous membrane, wherein said sample is present in an amount sufficient to cause the sample liquid to flow by lateral flow through the indicator zones towards the absorption pad, the indicator zones comprising a first antibody, or a fragment thereof, directed against the one or more blood group antigens, and to cause the cell-bound analyte in the sample liquid to form a complex with the first antibody, or a fragment thereof, in the indicator zones;
    visually detecting formation of the complex in the indicator zones.

11. The device according to claim 1, wherein the indicator zone is open to visual inspection such that presence of the complex can be visually identified.

12. A device for simultaneously determining a first and a second cell-bound analyte in a liquid sample, comprising:
    a porous membrane having a work zone for application of the liquid sample,
    at least two indicator zones which are able to interact with the cell-bound analytes, and
    at least one absorption pad a portion of which is in contact with a portion of the porous membrane such that the absorption pad absorbs the liquid sample after it has passed by lateral flow through the at least two indicator zones, the at least two indicator zones being situated between the work zone and the at least one absorption pad,
    wherein:
    (i) the first indicator zone comprises a first antibody, or a fragment thereof, directed against the cell-bound analyte, and a binding element directed against the first antibody, the first antibody being an incomplete antibody, and (ii) the second indicator zone comprises:
- (a) a first antibody directed against the second cell-bound analyte, the first antibody being a complete antibody; or
- (b) a first antibody directed against the second cell-bound analyte, the first antibody being incomplete, and a binding element directed against that first antibody, wherein the cell-bound analyte is a blood group antigen.

13. The device according to claim 12, wherein the first antibody in the first indicator zone (i) and/or the first antibody in the second indicator zone (ii) is an antibody of the IgG or IgA type.

14. The device according to claim 12, wherein the binding element directed against the first antibody in the first indicator zone (i) and/or in the second indicator zone (ii) is selected from an antibody directed against the first antibody, or a fragment thereof, and a lectin or a fragment thereof.

15. The device according to claim 14, wherein the binding element is an anti-IgG or anti-IgA antibody or the lectin is protein A or protein G.

16. The device according to claim 12, wherein the first antibody directed against the first cell-bound analyte and the binding element directed against the first antibody in the first indicator zone (i) and/or the first antibody directed against the second cell-bound analyte and the second binding element directed against the first antibody in the second indicator zone (ii) are IgG antibodies.

17. The device according to claim 12, wherein the second indicator zone (ii) comprises an IgM antibody directed against the second cell-bound analyte.

* * * * *